(12) United States Patent
Fowler et al.

(10) Patent No.: US 6,494,876 B1
(45) Date of Patent: Dec. 17, 2002

(54) DISPOSABLE LIPOSUCTION DEVICE AND METHOD

(75) Inventors: Reginald H. Fowler, Meridian, TX (US); Garrett L. Barker, Meridian, TX (US)

(73) Assignee: Byron Medical, Inc., Tucson, AZ (US)

( * ) Notice: Subject to any disclaimer, the term of this patent is extended or adjusted under 35 U.S.C. 154(b) by 0 days.

(21) Appl. No.: 09/570,990

(22) Filed: May 15, 2000

(51) Int. Cl.[7] .................................................. A61M 1/00
(52) U.S. Cl. .......................................... 604/542; 604/35
(58) Field of Search .......................... 604/542, 35, 22; 606/49; 607/118

(56) References Cited

U.S. PATENT DOCUMENTS

| | | | |
|---|---|---|---|
| 4,314,560 A | 2/1982 | Helfgott et al. | |
| 4,324,243 A | 4/1982 | Helfgott et al. | |
| 4,609,368 A | 9/1986 | Dotson, Jr. | |
| 4,650,460 A | 3/1987 | Roizenblatt | |
| 4,735,604 A | 4/1988 | Watmough et al. | |
| 4,735,605 A | 4/1988 | Swartz | |
| 4,753,634 A | 6/1988 | Johnson | |
| 4,775,365 A | 10/1988 | Swartz | |
| 4,792,327 A | 12/1988 | Swartz | |
| 4,815,462 A | 3/1989 | Clark | |
| 4,838,281 A | 6/1989 | Rogers et al. | |
| 4,909,249 A | 3/1990 | Akkas et al. | |
| 4,932,935 A | 6/1990 | Swartz | |
| 4,986,827 A | 1/1991 | Akkas et al. | |
| 5,013,300 A | 5/1991 | Williams | |
| 5,236,414 A | 8/1993 | Takasu | |
| 5,244,458 A | 9/1993 | Takasu | |
| 5,263,480 A | * 11/1993 | Wernicke et al. | 607/118 |
| 5,352,194 A | * 10/1994 | Greco et al. | 604/35 |
| 5,419,761 A | * 5/1995 | Natayanan et al. | 604/22 |
| 5,569,178 A | 10/1996 | Henley | |
| 5,609,602 A | 3/1997 | Machemer et al. | |
| 5,833,643 A | 11/1998 | Ross et al. | |
| 5,902,264 A | 5/1999 | Toso et al. | |
| 5,911,700 A | 6/1999 | Mozsary et al. | |
| 6,113,569 A | * 9/2000 | Becker | 604/35 |
| 6,213,971 B1 | * 4/2001 | Poole | 604/35 |
| 6,336,925 B1 | * 1/2002 | Malak | 604/542 |
| 6,346,107 B1 | * 2/2002 | Cucin | 606/49 |

FOREIGN PATENT DOCUMENTS

FR   2700958   * 8/1994   ............ A61M/1/00

* cited by examiner

*Primary Examiner*—Teresa Walberg
*Assistant Examiner*—Leonid M. Fastovsky
(74) *Attorney, Agent, or Firm*—Birdwell, Janke & Durando, PLC

(57) ABSTRACT

A disposable liposuction device and method. A piston is caused to reciprocate by operating a single valve. The electrical energy for operating the valve is provided by an electric timing circuit that is powered by a battery. The energy provided by the battery is predetermined so that the energy is depleted after about the time required for one liposuction procedure.

14 Claims, 3 Drawing Sheets

DISPOSABLE LIPOSUCTION DEVICE AND METHOD

BACKGROUND OF THE INVENTION

The present invention relates to a disposable liposuction device and method. Liposuction is a procedure for removing fatty tissue from the body. A cannula is inserted into the body and moved back and forth to break-up the fatty tissue. The cannula may be attached to a hand-held liposuction device which reciprocates the cannula for this purpose. The device is coupled to a vacuum pump to provide suction for removing the tissue once it is broken up by the reciprocating action of the cannula. For reciprocating the cannula, a rotating device may be employed in the liposuction device wherein rotary motion is converted to reciprocating motion by a crankshaft. A simpler alternative, however, is to employ a two-sided piston operated by a fluid under pressure, e.g., air, applied alternately to each side of the piston through respective valves. The valves add complexity to the device and require a power source for their operation. Such a power source should be capable of powering the device for up to about 12 hours for one liposuction procedure and typically must be provided externally of the device due to the weight and size of the power source required. In addition, fluid applied to one side of the piston, to force the piston in one direction, typically must be exhausted so that fluid applied to the other side of the piston can be effective to force the piston in the opposite direction, representing a consumption of the compressed or pressurized fluid which it would be desirable to minimize.

Liposuction devices are typically designed to be autoclaved so that they can be reused for many procedures. However, to adapt the liposuction device for multiple uses, including to adapt the device for the autoclave, greatly increases its cost. The present inventor has recognized that it would be desirable to reduce the cost of the liposuction device sufficiently to justify disposing it at the end of the procedure.

However, even if this were accomplished, the concept introduces the problem of ensuring that such disposal will occur.

Another problem with the prior art that the suction conduit used for carrying off the fatty tissue from the body is attached to the device so that it reciprocates with the cannula. This makes the device more difficult for the surgeon to handle and control during use.

Accordingly, there is a need for a disposable liposuction device and method that provides for the decreased cost of fabrication necessary to justify using the device for just one procedure, that provides for ensuring that the device will be used for only one procedure, and that provides for increased ease of use.

SUMMARY OF THE INVENTION

The disposable liposuction device and method of the present invention solves the aforementioned problems and meets the aforementioned needs by providing a reciprocating member operated by a single valve member. The reciprocating member has two opposite surfaces. One of the surfaces is in constant fluid communication with a pressurized fluid supply and the other surface is in fluid communication with a pressurized fluid supply through the valve member. The valve member has a normal position, either open or closed, and can be switched to move to the alternate of these two positions by providing power, wherein the valve member returns to its normal position when power is no longer being provided.

The power for switching the valve member is provided by an electric timing circuit that is powered by a battery. The battery is preferably incorporated in a housing provided for housing the device, the housing being adapted to be held by an operator of the device. The electrical timing circuit and battery are adapted so that the battery provides enough energy to power the device during the time required for one procedure, and that this energy is substantially depleted after such time.

The reciprocating member reciprocates relative to the housing. A chamber is preferably provided in the housing, the reciprocating member being adapted to move back and forth within the chamber over the length of its stroke. The chamber provides a seal that maintains fluid pressure on the reciprocating member and decouples the reciprocating member from a suction lumen provided in the apparatus for carrying the fatty tissue out of the device.

The device also preferably includes alignment members for preventing the reciprocating member from rotating axially.

Therefore, it is a principal object of the present invention to provide a novel and improved disposable liposuction device and method.

It is another object of the present invention to provide a disposable liposuction device and method that provides for the decreased cost of fabrication necessary to justify using the device for just one procedure.

It is still another object of the present invention to provide a disposable liposuction device and method that provides for exhaustion of the device after one procedure, to ensure that the device will not be reused.

It is yet another object of the present invention to provide a disposable liposuction device and method that provides for increased ease of use.

The foregoing and other objects, features and advantages of the present invention will be more readily understood upon consideration of the following detailed description of the invention, taken in conjunction with the following drawings.

DETAILED DESCRIPTION OF A PREFERRED EMBODIMENT

Figure 1:
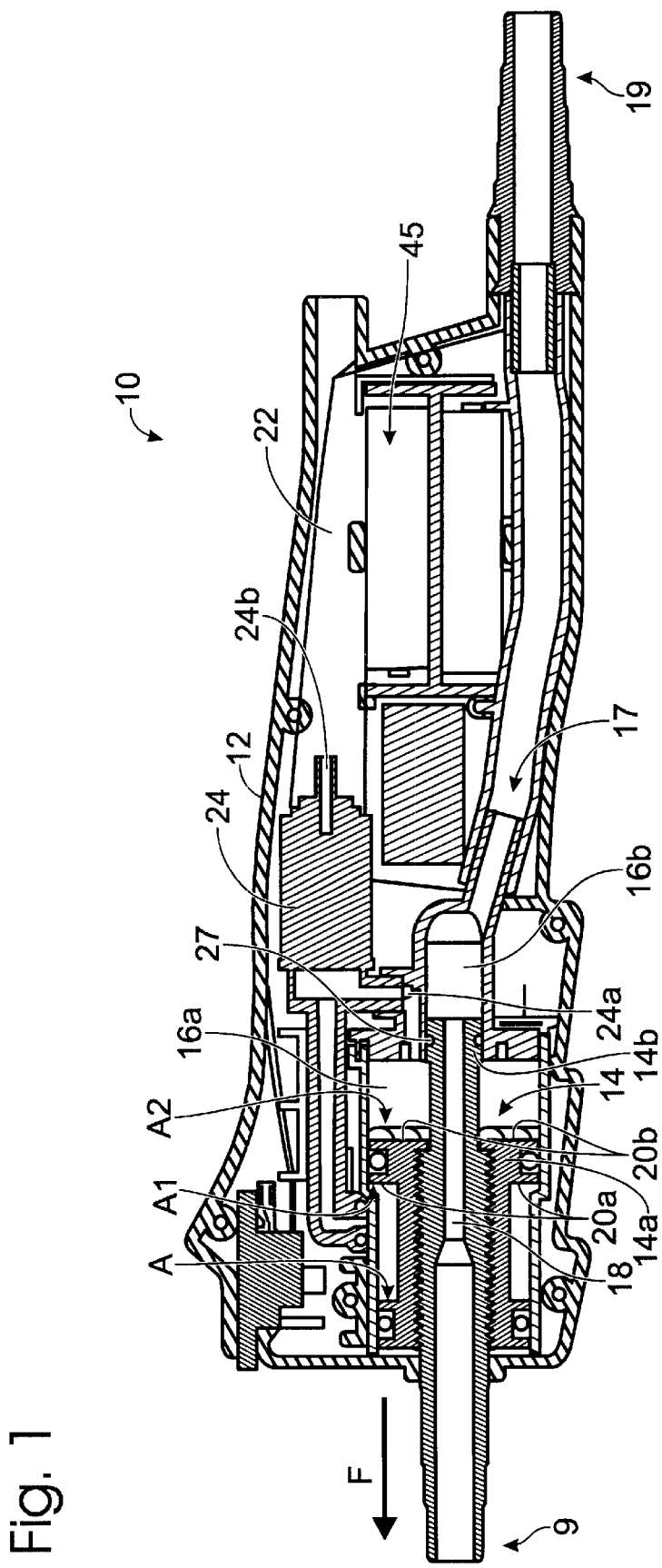
FIG. 1 is a side section of a disposable liposuction device according to the present invention showing a piston at the completion of a forward stroke.

Referring to Figure, a disposable liposuction device 10 according to the present invention is shown. While the device 10 is adapted particularly for use in liposuction, the principles of the invention apply to any device and method wherein it is desired to provide either suction or pressurization. Moreover, while features of the device 10 provide for the outstanding advantage that the device is disposable, there is no intention to limit the invention where its principles have broader applicability.

The device 10 includes a first connector 9 for attaching a cannula (not shown) which is intended to be inserted into a patient's body through an incision. The device includes a housing 12 that is adapted to be held by an operator of the device. The housing contains a piston 14 which is disposed in a two part chamber 16 at 16a and 16b. The piston 14 includes a lumen 18 which is in fluid communication with, at one end, the connector 9 and cannula and, inside the housing downstream of the piston, a suction lumen 17 for carrying fatty tissue passed through the lumen 18 downstream, out of the device 10. The device includes a connector 19 for attaching a hose (not shown) which is connected at its other end to a vacuum pump providing suction for urging the fatty tissue from the patient, through and away from the device as described, to a final point of collection.

The piston 14 further includes a pressure receiving portion 14a, which is disposed within the chamber 16a. This pressure receiving portion has two annular sides 20a and 20b. As explained more fully below, reciprocating action is produced by providing a fluid at a substantially constant pressure on one of the sides, and providing a fluid at a selected variable pressure on the other side.

Figure 2:
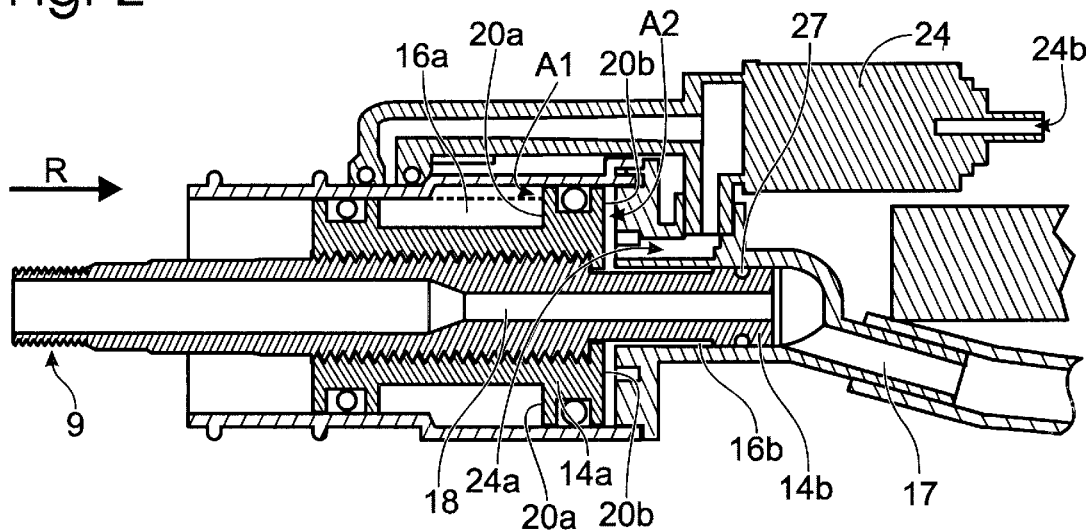
FIG. 2 is a side section of the liposuction device of FIG. 1, showing the piston at the completion of a return stroke.

More particularly, the side 20a of the piston is in constant fluid communication with a source 21 (not shown) of fluid, preferably air, at a substantially constant gauge pressure "P". This provides for a substantially constant force on the side 20a of the piston. This force is equal to the source pressure P multiplied by the "effective"annular area Al of the side 20a. In FIG. 1, it can be seen that the effective area A1 accounts for subtracting the area A on an opposite side of the chamber 16a that corresponds in size to the remaining area on the side 20a. FIG. 2 shows this area more clearly, as being the area on the side 20a that is above the dotted line.

The device also includes a solenoid operated valve 24 that has a port 24a in fluid communication with the side 20b of the piston 14. The valve 24 may be connected to another source of pressurized fluid; however, it is preferably also connected to the source 21. The port 24a is preferably normally closed and the valve is energized to open the port and thereby provide a fluid path through the valve to the side 20b of the piston. The valve is energized by supplying electrical current to a solenoid in the valve, as explained more fully below.

The valve 24 also includes an exhaust port 24b that is normally open, the exhaust port being connected to an exhaust lumen 22 leading to the exterior ofthe device. Where the working fluid is air, the exhaust port may simply open to the atmosphere as shown. When the valve 24 is energized to open the port 24a, to permit the source 21 to provide fluid pressure to the side 20b of the piston, the exhaust port 24b is closed during the same time. The fluid provides a pressure on the side 20b that is equal to the pressure P multiplied by the annular area A2 of the side 20b.

Accordingly, before the valve 24 is energized, the piston has net force of(P)•(A1) pushing the piston in the "return" direction "R" as indicated in FIG. 2, and after the valve is energized, the piston has a net force of (P)•(A2−A1) pushing the piston in the opposite, "forward" direction as indicated in FIG. 1. Provided that the area A2 is larger than the area Al,the piston will reciprocate at the frequency that the valve is energized and de-energized. In the preferred embodiment, with a source pressure of 60 psi, the area A1 is adjusted so that (P)•(A1)=12 pounds, and the area A2 is adjusted so that (P)•(A2)=52 pounds, providing a 40 pound forward stroke and a 12 pound return stroke.

To illustrate the reciprocating action, FIG. 1 shows the piston at the full length of its forward stroke and FIG. 2 shows the piston at the full length of its return stroke. The use of a single action pneumatic valve provides a number of advantages, including mechanical simplicity and therefore economy, and the use of a pressurized fluid provides for a constant return force over the stroke of the piston 14, a highly desirable feature in a liposuction device that is not provided, for example, by spring biasing means.

The piston 14 also includes an extension portion 14b which sealingly engages, through O-ring 27, the chamber 16b. While the pressure receiving portion 14a of the piston reciprocates within the chamber 16a, the extension portion 14b extends into and reciprocates in the chamber 16b. Moreover, the O-ring 27 ensures that the chamber 16b is sealed from the chamber 16a over the entire stroke of the piston 14, to maintain pressure developed in the latter. Moreover, the chamber 16b is stationary with respect to the housing 12 so that the suction lumen 17 is decoupled from the reciprocating motion of the piston.

It is not essential to the invention that the device 10 be disposable. However, the principles described above facilitate reducing the cost of the device sufficiently to justify disposing of the device after one procedure, which provides an outstanding advantage over the prior art. Particularly, the use of a single valve 24 to drive the piston 14 in two opposite directions simplifies construction of the device, and the reduced power requirement of single valve operation makes a disposable liposuction device even more practical.

On the other hand, the inventor has recognized that a cost reduced liposuction device that omits the capability for autoclave in the interest of achieving even greater economy could pose a health risk if the device were to be reused by mistake. This has led to yet another recognition that, if the power requirements for the device are reduced sufficiently that it becomes practical to power the device from an internal battery that is of reasonable size and weight for use in a hand-held liposuction device, the energy stored in this battery can be predetermined so that depletion of the battery is provided after a time that allows for the completion of one procedure.

The power requirements of the device have been reduced according to the present invention in two primary ways. First, the use of a single valve 24 to operate the piston cuts the power requirements approximately in half. Second, an electrical circuit 30 (FIG. 3) is provided for driving the valve that provides for minimum energy consumption thereby. These measures each contribute to permitting the use of a battery that is not too large or heavy to be practical in a hand-held and hand-operated liposuction device.

Figure 3:
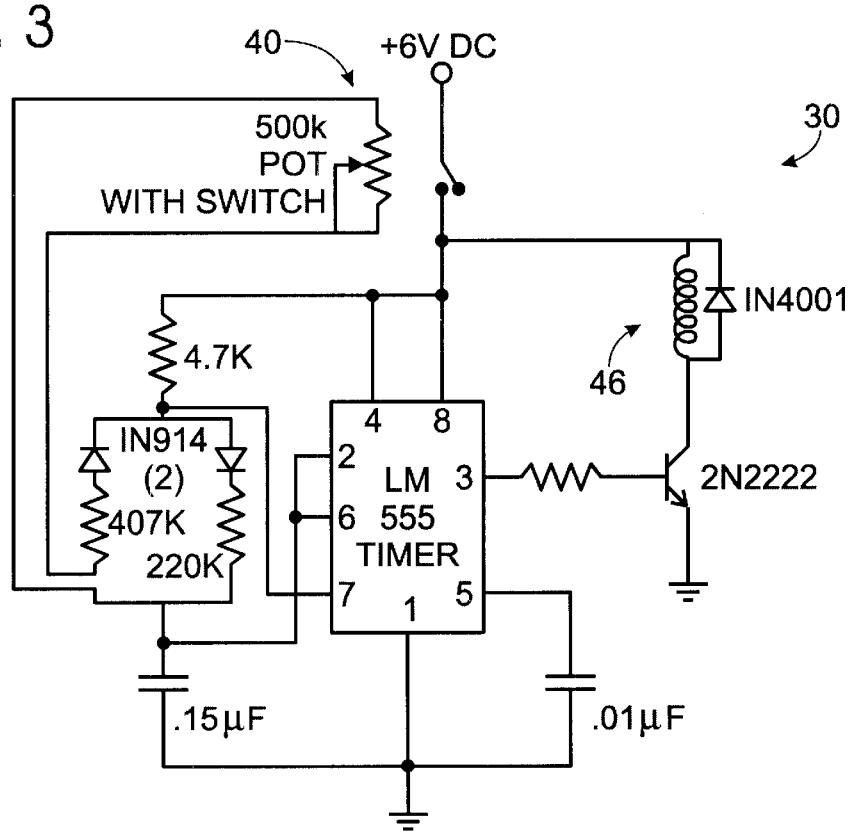
FIG. 3 is a schematic of an electrical circuit for energizing the device of FIG. 1, according to the present invention.

In the preferred device 10, the valve 24 includes a solenoid for opening the port 24a, and closing the port 24b by the same action, which is operated by an electrical timing circuit 30 as shown in FIG. 3 providing for a reciprocation frequency between about 400 to about 800 cycles per minute. The circuit of FIG. 3 is believed to provide maximum simplicity and economy; however, many alternative means for providing the required reciprocation, such as by using a pulse generator, a microprocess or computer, may be employed without departing from the principles of the invention.

The preferred circuit is built around a standard 555 timer for periodically energizing a solenoid 46 in the valve 24. It has been determined that a sufficient duration for the current pulse is about 20 ms. At 800 cycles per minute (75 ms/cycle), this leaves 55 ms to exhaust that portion of the chamber 16a that is on the side 20b of the piston. For lower frequencies of reciprocation, set by the potentiometer 40, the energizing pulse advantageously remains at 1 ms to minimize power requirements and the time for exhaust during which there is no appreciable current provided to the valve 24 is commensurately increased. Preferably, 4 AAA alkaline batteries 45 provide power to the electrical circuit 30, providing for operation of the device 10 for about 12 hours of reciprocation at 800 cycles per minute, or about 575,000 cycles.

Figure 4:
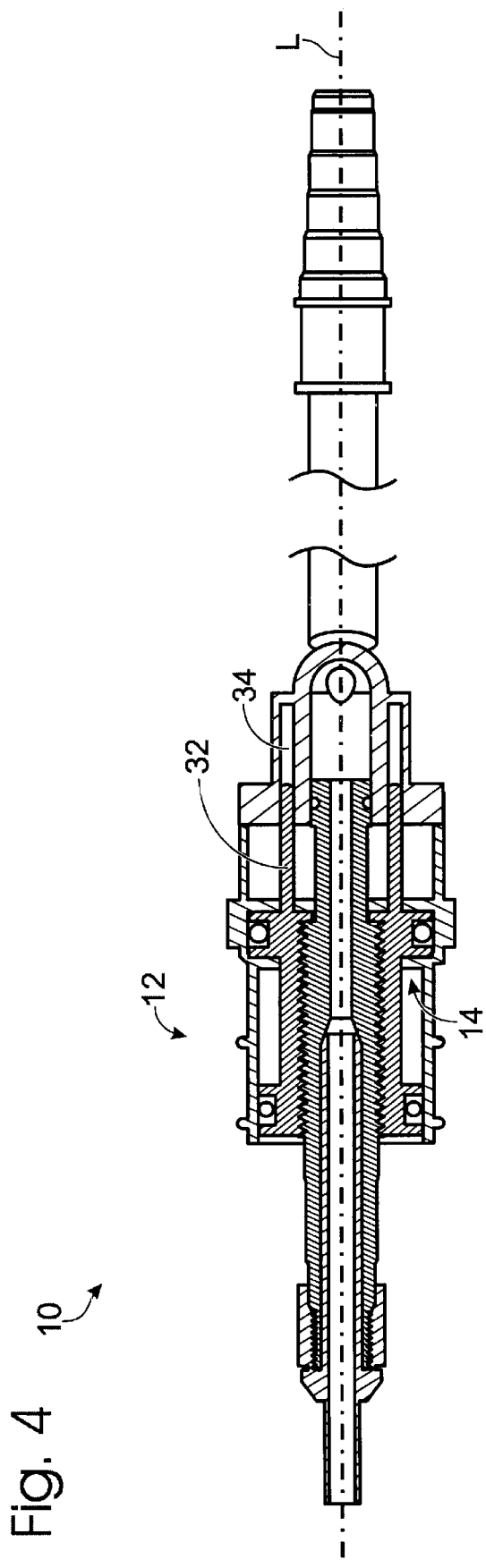
FIG. 4 is a top section of the liposuction device of FIG. 1, showing alignment members according to the present invention.

Turning to FIG. 4, a top section of the device 10 shows alignment members 32 that extend from the piston 14 and are received by corresponding slots 34. The alignment members and slots prevent the piston 14 from rotating axially, i.e., about the axis "L" of reciprocation. This permits using a cannula having a side aperture and maintaining the orientation of the side aperture with respect to the housing 12.

It is to be recognized that, while a particular disposable liposuction device and method has been shown and described as preferred, other configurations could be utilized, in addition to configurations already mentioned, without departing from the principles of the invention. As has been mentioned, while the features of the invention provide for making the device disposable, this is not essential to the invention.

Moreover, the minimum power consumption that facilitates making the invention disposable results both from the use of a minimum valve arrangement as well as by employing a minimum activation energy for the valve. However, while it is best to employ both of these principles together, this is not essential to realize practical advantages according to the invention.

The terms and expressions which have been employed in the foregoing specification are used therein as terms of description and not of limitation, and there is no intention of the use of such terms and expressions of excluding equivalents of the features shown and described or portions thereof, it being recognized that the scope of the invention is defined and limited only by the claims which follow.

What is claimed is:

1. A liposuction device, comprising a reciprocating member having two opposite surfaces, wherein one of said surfaces is in fluid communication with a first source of fluid under a first pressure that is greater than ambient pressure through a valve that is switchable between a first configuration in which said fluid is permitted to flow through said valve and a second configuration in which said fluid is substantially blocked from flowing through said valve, wherein the other of said surfaces is in fluid communication with a source of pressurized fluid at a substantially fixed second pressure that is greater than ambient pressure, and a control device operatively connected to said valve for switching said valve between said first and second configurations, wherein the areas of said two opposite surfaces and said pressures are selected in combination so that said reciprocating member reciprocates in response to said valve being switched.

2. The liposuction device of claim 1, wherein said first and said second source of fluid are the same source of fluid, and wherein said first pressure and said second pressure are substantially equal.

3. The liposuction device of claim 1, wherein said valve is normally in said second configuration and wherein said control mechanism must provide energy to said valve to maintain said valve in said first configuration.

4. The liposuction device of claim 3, wherein said control device includes an electrical circuit that supplies electrical current to said valve to maintain said valve in said first configuration.

5. The liposuction device of claim 4, further comprising a battery housed in a housing that contains said reciprocating member for providing the electrical power needed by said electrical circuit to maintain said valve in said first configuration.

6. The liposuction device of claim 4, wherein said electrical circuit is adapted to supply a pulse of electrical current having a duration of about 20 ms.

7. The liposuction device of 6, wherein said electrical circuit is adapted to provide for repeating said pulse of electrical current at an adjustable frequency.

8. The liposuction device of claim 5, wherein said battery is adapted to provide sufficient power to power the device for about 12 hours of operation at about 800 cycles per minute.

9. The liposuction device of claim 8, wherein said battery is adapted to be substantially depleted after said duration of time.

10. The liposuction device of claim 1, wherein said reciprocating member includes an extension portion extending from one of said surfaces in the direction of reciprocation, said extension portion sealingly engaging a chamber for receiving said extension portion.

11. The liposuction device of claim 1, further comprising alignment members extending from said reciprocating member for preventing said reciprocating member from rotating axially.

12. A method for liposuction, comprising providing a hand-held liposuction device containing a reciprocating member having two opposite surfaces, wherein one of said surfaces is in fluid communication with a first source of fluid under a first pressure that is greater than ambient pressure through a valve that is switchable between a first configuration in which said fluid is permitted to flow through said valve and a second configuration in which said fluid is substantially blocked from flowing through said valve, wherein the other of said surfaces is in fluid communication with a source of pressurized fluid at a substantially fixed second pressure that is greater than ambient pressure, an electrical circuit operatively connected to said valve for switching said valve between said first and second configurations, and a battery for powering said electrical circuit.

13. The method of claim 12, further comprising producing a current pulse by said electrical circuit for switching said valve, said current pulse having a duration of about 20 ms.

14. The method of claim 12, further comprising producing a plurality of current pulses by said electrical circuit each having a duration of about 20 ms and varying the frequency of said current pulses to vary the frequency of said reciprocating member.

* * * * *